US005830450A

United States Patent [19]
Lallone

[11] Patent Number: 5,830,450
[45] Date of Patent: Nov. 3, 1998

[54] COMPOSITIONS OF LEPTIN BOUND TO AN APOLIPOPROTEIN

[76] Inventor: Roger L. Lallone, 2924 Jamamie La., Birmingham, Ala. 35243

[21] Appl. No.: 666,805

[22] Filed: Jun. 19, 1996

[51] Int. Cl.$^6$ .................................................. A61K 38/00
[52] U.S. Cl. .............................. 424/85.1; 514/2; 530/350; 530/351; 530/402; 530/359; 435/7.1
[58] Field of Search ................................. 514/2; 530/350, 530/351, 402, 359; 424/9.1, 9.34, 85.1; 435/7.1

[56] References Cited

FOREIGN PATENT DOCUMENTS 9706816  2/1997  WIPO .

OTHER PUBLICATIONS

Frederich et al, *Nature Medicine* 12, 1995, p. 1311.
Houscknecht et al, *Diabetes* 1996, 45, 1638–43.
Sinha et al, *J Clin Invest* 98(6) 1996, p. 1277.
Campfield et al. Science 269: 546–49, 1995.
Zlokovic et al. Biochem. Biophys Res Comm. 205(2):1431–37, Dec. 15, 1994.
Barinaga, Marcia, "'Obese' Protein Slims Mice," *Science* 269:475–476 (1995).
Campfield, L. Arthur et al., "Recombinant Mouse OB Protein: Evidence for a Peripheral Signal Linking Adiposity and Central Neural Networks," *Science* 269:546–549 (1995).
Choi–Miura, Nam–Ho, "Beta–Endorphin Binding Activity of SP–40,40," *Biol. Pharm. Bull.* 16(3):228–231 (1993).
Pelleymounter, Mary Ann et al., "Effects of the obese Gene Product on Body Weight Regulation in ob/ob Mice," *Science* 269:540–543 (1995).
Jenkins, Sarah H. et al., "Quantitation of Plasma Apolipoprotein J," *Methods in Enzymology* 263:309–316.
Zlokovic, Berislav V. et al., "Brain Uptake of Circulating Apolipoproteins J and E Complexed to Alzheimer's Amyloid B$^1$," *Biochemical and Biophysical Research Communications* 205(2):1431–1437 (1994).
Halaas, Jeffrey L. et al., "Weight–Reducing Effects of the Plasma Protein Encoded by the obese Gene," *Science* 269:543–546 (Jul. 1995).
Maffei, M. et al., "Leptin levels in human and rodent: Measurement of plasma leptin and ob RNA in obese and weight–reduced subjects," *Nature Medicine* 1(11):1155–1161 (Nov. 1995).

*Primary Examiner*—Garnette D. Draper
*Attorney, Agent, or Firm*—David A. Farah; Sheldon & Mak

[57] ABSTRACT

A composition for diagnosing or treating abnormalities in the endogenous leptin pathway in a subject mammal consisting essentially of apolipoprotein J bound to leptin or comprising a purified form of apolipoprotein J bound to leptin. A method for diagnosing abnormalities in the endogenous leptin pathway in a subject mammal. A method for treating abnormalities in the endogenous leptin pathway in a subject mammal. A method for determining the presence or amount of leptin that is associated with apolipoprotein J in a test sample. A kit for performing the method for determining the presence or amount of leptin that is associated with apolipoprotein J in a test sample.

13 Claims, 10 Drawing Sheets

| AN | 0.014 | 0.896 | 0.191 | 0.62 |
|----|-------|-------|-------|------|
| AN | 0.114 | 0.959 | 0.126 | 0.345 |
| AN | 0.227 | 1.029 | 0.076 | 0.473 |
| AN | 0.057 | 0.913 | 0.09 | 0.504 |
| AN | 0.041 | 0.89 | 0.043 | 0.433 |
| AN | 0.044 | 0.836 | 0.035 | 0.445 |
| AN | 0.127 | 0.837 | 0.53 | 0.374 |
| NO | 0.184 | 0.92 | 0.019 | 0.672 |
| NO | 0.281 | 0.969 | 0.048 | 0.679 |
| NO | 0.127 | 0.984 | 0.289 | 0.688 |
| NO | 0.231 | 0.898 | 0.059 | 0.637 |
| NO | 0.278 | 0.947 | 0.299 | 0.616 |

| OB | 0.21 | 0.36 | 0.226 | 0.529 |
|----|------|------|-------|-------|
| OB | 0.259 | 0.361 | 0.562 | 0.643 |
| OB | 0.485 | 0.382 | 1.249 | 0.508 |
| OB | 0.308 | 0.443 | 1.509 | 0.614 |
| OB | 0.336 | 0.52 | 1.583 | 0.986 |
| OB | 0.209 | 0.568 | 1.191 | 0.62 |
| OB | 0.36 | 0.424 | 1.051 | 0.388 |
| OB | 0.246 | 0.382 | 0.589 | 0.588 |
| PW | 0.4 | 0.448 | 1.113 | 0.528 |
| PW | 0.33 | 0.514 | 0.864 | 0.384 |
| PW | 0.29 | 0.395 | 0.782 | 0.559 |
| PW | 0.309 | 0.319 | 0.674 | 0.493 |

COMPOSITIONS OF LEPTIN BOUND TO AN APOLIPOPROTEIN

BACKGROUND

Obesity is a condition characterized by excessive adipose tissue. The presence and degree of obesity are usually determined by reference to the absolute weight of an individual when compared to age and height matched ideals, or by reference to the individual's body mass index, that is, body weight (in kilograms) divided by height (in meters$^2$), compared with age matched ranges. Obesity is associated with decreased life expectancy and contributes to a myriad of diseases and conditions. These include diabetes, heart disease and hypertension.

The underlying physiologic cause of most obesity has remained obscure. However, a blood-borne protein designated "leptin" has been identified which is produced by adipose tissue from a gene designated the "obese gene." Leptin is present in mammals, including mice and humans, and is a monomer of approximately 16 kDa.

Mice that produce no functional leptin due to a mutation in the obese gene, the ob/ob genotype, have an obese phenotype. Administration of exogenous human or mouse leptin to such ob/ob mice results in decreased food intake and weight reduction. It is possible, therefore, that leptin is a hormone that functions to control the amount of adipose tissue through a negative feedback pathway.

However, studies of human leptin levels in normal and obese individuals using currently known methods appear to suggest that leptin levels are increased in obese individuals rather than decreased. The studies further suggest that most obese individuals do not appear to have defective copies of the obese gene. Hence, currently available methods do not appear useful for indicating whether a defect exists in the endogenous leptin pathway of any particular individual.

Therefore, it would be advantageous to have a method and composition useful in detecting physiological obesity and other conditions related to abnormalities of the endogenous leptin pathway. Also, it would be advantageous to have a method and composition useful in treating physiological obesity and other conditions related to abnormalities of the endogenous leptin pathway.

SUMMARY

According to one embodiment of the present invention, there is provided a composition for diagnosing or treating abnormalities in the endogenous leptin pathway in a subject mammal consisting essentially of apolipoprotein J bound to leptin. According to another embodiment of the present invention, there is provided a composition for diagnosing or treating abnormalities in the endogenous leptin pathway in a subject mammal comprising a purified form of apolipoprotein J bound to leptin. Either of these compositions can be derived from a recombinant source, can be from a mammal or can be from a human.

According to another embodiment of the present invention, there is provided a pharmaceutical preparation for diagnosing or treating abnormalities in the endogenous leptin pathway in a subject mammal comprising a purified form of apolipoprotein J bound to leptin and a pharmaceutically acceptable carrier. According to another embodiment of the present invention, there is provided a pharmaceutical preparation for diagnosing or treating abnormalities in the endogenous leptin pathway in a subject mammal consisting essentially of apolipoprotein J bound to leptin, and a pharmaceutically acceptable carrier. According to another embodiment of the present invention, there is provided a pharmaceutical preparation for diagnosing or treating abnormalities in the endogenous leptin pathway in a subject mammal comprising apolipoprotein J and a pharmaceutically acceptable carrier, with or without leptin.

According to another embodiment of the present invention, there is provided a method of making the compositions disclosed herein, comprising the steps of, first, providing an amount of substantially purified leptin, and then binding the leptin to apolipoprotein J. The leptin can be derived from a recombinant source, can be from a mammal or can be from a human. The method can further comprise a step of adding a pharmaceutically acceptable carrier.

According to another embodiment of the present invention, there is provided a method for diagnosing abnormalities in the endogenous leptin pathway in a subject mammal comprising the steps, first determining an amount of apolipoprotein J in a test sample taken from the subject mammal, and then comparing the determined amount to a range of values for mammals with normal endogenous leptin pathways, wherein a determined amount greater than or less than the range of values indicates a diagnosis of an abnormality in the endogenous leptin pathway.

According to another embodiment of the present invention, there is provided a method for diagnosing physiological obesity in a subject mammal comprising the steps of, first, determining an amount of apolipoprotein J in a test sample taken from the subject mammal, and then, comparing the determined amount to a range of values for mammals with normal endogenous leptin pathways, wherein a determined amount less than the range of values indicates a diagnosis of physiological obesity.

According to another embodiment of the present invention, there is provided a method for diagnosing abnormalities in the endogenous leptin pathway in a subject mammal comprising the steps of, first, determining an amount of leptin bound to apolipoprotein J in a test sample taken from the subject mammal, and then comparing the determined amount to a range of values for mammals with normal endogenous leptin pathways, wherein a determined amount greater than or less than the range of values indicates a diagnosis of an abnormality in the endogenous leptin pathway.

According to another embodiment of the present invention, there is provided a method for diagnosing physiological obesity in a subject mammal comprising the steps of, first determining an amount of leptin bound to apolipoprotein J in a test sample taken from the subject mammal, and then comparing the determined amount to a range of values for mammals without physiological obesity, wherein a determined amount less than the range of values indicates a diagnosis of physiological obesity.

According to another embodiment of the present invention, there is provided a method for diagnosing abnormalities in the endogenous leptin pathway in a subject mammal comprising the steps of, first, determining at least one parameter in a test sample taken from the subject mammal selected from the group consisting of 1) an absolute amount of leptin bound to apolipoprotein J, 2) an absolute amount of leptin not bound to apolipoprotein J, 3) a percent of total leptin that is bound to apolipoprotein J, 4) a percent of total leptin that is not bound to apolipoprotein J, 5) the ratio of (an absolute amount of leptin that is bound to apolipoprotein J) to (an absolute amount of total leptin), 6) the ratio of (an absolute amount of leptin that is bound to apolipoprotein J) to (an absolute amount of leptin that is not bound to apolipoprotein J), and 7) the ratio of (an absolute amount of leptin that is not bound to apolipoprotein J) to (an absolute amount of total leptin), and then, comparing the determined parameter with a range of values for the parameter in the same type of mammal without abnormalities in the endogenous leptin pathway wherein a determined amount lesser or greater than the range of values indicates a diagnosis of an abnormality in the endogenous leptin pathway.

According to another embodiment of the present invention, there is provided a method for treating abnormalities in the endogenous leptin pathway in a subject mammal comprising the step of administering at least one dose of a composition comprising apolipoprotein J or comprising the step of administering at least one dose of a composition comprising leptin bound to apolipoprotein J, or comprising the step of administering at least one dose of a composition according to the present invention. The method can further comprise the step of serially monitoring an amount of leptin bound to apolipoprotein J in a test sample taken from the subject mammal after the step of administering or can further comprise the step of serially monitoring at least one parameter in a test sample taken from the subject mammal selected from the group consisting of 1) an absolute amount of leptin bound to apolipoprotein J, 2) an absolute amount of leptin not bound to apolipoprotein J, 3) a percent of total leptin that is bound to apolipoprotein J, 4) a percent of total leptin that is not bound to apolipoprotein J, 5) the ratio of (an absolute amount of leptin that is bound to apolipoprotein J) to (an absolute amount of total leptin), 6) the ratio of (an absolute amount of leptin that is bound to apolipoprotein J) to (an absolute amount of leptin that is not bound to apolipoprotein J), 7) the ratio of (an absolute amount of leptin that is not bound to apolipoprotein J) to (an absolute amount of total leptin), and 8) a combination of the preceding.

According to another embodiment of the present invention, there is provided a method for determining the presence or amount of leptin that is associated with apolipoprotein J in a test sample comprises the steps of, first, providing a support having a first binding substance thereon, the first binding substance capable of binding leptin associated with apolipoprotein J to the support. Then, the support is contacted with the test sample, thereby allowing any leptin associated with apolipoprotein J in the test sample to bind to the support through the first binding substance. Then, the support is contacted with a second binding substance, where the second binding substance is capable of binding to any leptin associated with apolipoprotein J that has bound to the support, or that is capable of binding to the first substance only when leptin associated with apolipoprotein J has bound to the first binding substance. Then, the second binding substance is detected, wherein the detected second binding substance correlates with presence or amount of leptin associated with apolipoprotein J. The first binding substance in step (a) can be, for example, selected from the group consisting of an anti-leptin antibody, an anti-apolipoprotein J antibody, a fraction of an antileptin antibody, a fraction of an anti-apolipoprotein J antibody, a derivative of an anti-leptin antibody, a derivative of an anti-apolipoprotein J antibody and a combination of the preceding. The second binding substance in step (c) can be, for example, selected from the group consisting of an anti-leptin antibody, an anti-apolipoprotein J antibody, a fraction of an antileptin antibody, a fraction of an anti-apolipoprotein J antibody, a derivative of an anti-leptin antibody, a derivative of an anti-apolipoprotein J antibody and a combination of the preceding.

According to another embodiment of the present invention, there is provided a kit for performing a method according to the present invention comprising a support having the first binding substance, and a container holding the second binding substance. According to another embodiment of the present invention, there is provided a kit for performing a method according to the present invention comprising a container holding the first binding substance, and a container holding the second binding substance.

FIGURES

These features, aspects and advantages of the present invention will become better understood with regard to the following description, appended claims and accompanying figures where:

DESCRIPTION

Figure 1:
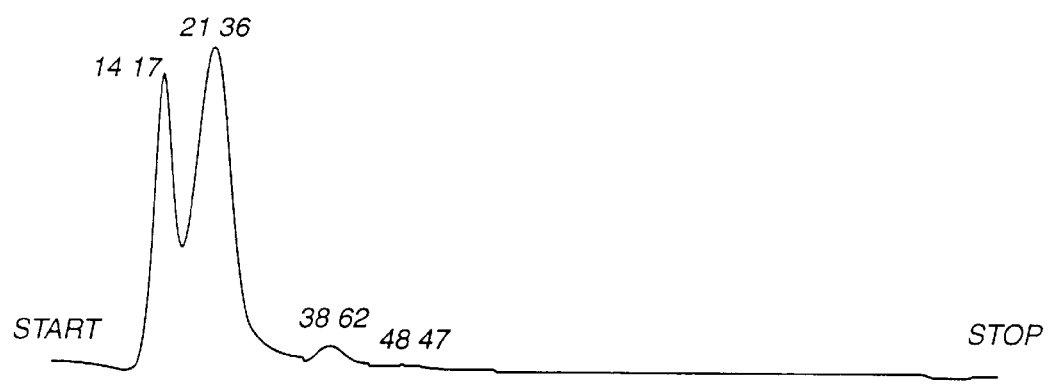
FIG. 1 is a continuous gel filtration profile under neutral phase conjugation of material containing human serum leptin that eluted off anti-leptin affinity columns.

Among other discoveries, the present invention is based on the discovery that at least part of blood borne leptin in mammals is bound to apolipoprotein J or a subclass of apolipoprotein J, and that, by virtue of the association between apolipoprotein J and HDL, at least part of blood borne leptin in mammals is bound to a lipoprotein complex.

In one embodiment, the present invention is a method and composition useful in detecting physiological obesity and other conditions related to abnormalities of the endogenous leptin pathway. In another embodiment, the present invention is a method and composition useful in treating physiological obesity and other conditions related to abnormalities of the endogenous leptin pathway. Further, the present invention includes methods of making the compositions according to the present invention.

As used herein, "physiological obesity" and "physiologically obese" refer to excessive adipose tissue that is due at least in part to abnormalities in the endogenous leptin pathway, including abnormalities in leptin quantity, form (such as proportion that is bound) or effect. The phrase "conditions related to abnormalities of the endogenous leptin pathway" encompasses conditions and diseases due, at least in part, to abnormalities in leptin quantity, form (such as proportion that is bound) or effect, such as abnormal food intake, activity level and body temperature.

The association between leptin and apolipoprotein J in the blood of humans and other mammals was demonstrated as abbreviated below and then described in greater detail as follows:

ABBREVIATED DESCRIPTION OF THE PURIFICATION AND IDENTIFICATION OF LEPTIN BINDING SUBSTANCE

1) Polyclonal anti-leptin antibodies were produced to recombinant human leptin, as well as to recombinant mouse leptin.
2) Leptin affinity columns were prepared.
3) The anti-leptin antibodies were purified using the leptin affinity columns.
4) Anti-leptin affinity columns were prepared using the purified anti-leptin antibodies.
5) The anti-leptin affinity columns were used to separate material containing leptin from human blood samples.
6) The material containing human leptin that was separated using the anti-leptin affinity columns was analyzed using gel filtration to separate the components by relative molecular weight, and fractions of the eluate were analyzed to determine their immunoreactivity to anti-leptin antibodies. It appeared that leptin in human blood is associated, at least in part, with at least one protein that was labeled "leptin binding substance."
7) The processes used to analyze leptin from human blood samples were repeated using mouse blood samples to determine whether mouse leptin was also associated with a corresponding binding substance in mouse serum. It appeared that mouse leptin was associated with a corresponding binding substance.
8) Human leptin binding substance was initially isolated and purified from human serum samples, and its molecular weight was determined.
9) Rabbit anti-human leptin binding substance antibodies were produced, affinity purified and cross-absorbed against a panel of normal human proteins.
10) Biotinylation of the rabbit anti-human leptin binding substance antibodies and HRP conjugation of streptavidin was performed.
11) Human leptin binding substance was purified using the biotinylated rabbit anti-human leptin binding substance antibodies in conjunction with SDS-PAGE and western blotting.
12) The purified human leptin binding substance was sequenced and the identity of the leptin binding substance was confirmed to be apolipoprotein J.

EXPANDED DESCRIPTION OF THE PURIFICATION AND IDENTIFICATION OF LEPTIN BINDING SUBSTANCE

1) Production of Polyclonal Anti-leptin Antibodies

Polyclonal antibodies to recombinant human leptin, as well as to recombinant mouse leptin were produced using New Zealand White rabbits, as follows. Each of these recombinant leptins has known amino acid sequences. One group of animals received priming injections consisting of 1–2 mg of recombinant human leptin emulsified in Freund's incomplete adjuvant and subsequent booster injections containing 0.25–0.50 mg of recombinant human leptin emulsified in Freund's incomplete adjuvant. Another group of animals received identical injections containing recombinant mouse leptin. The animals were maintained on a continuous injection-bleed-rest cycle, approximately six weeks in length. Between 25–50 ml of blood was collected from the proximal ear vein of each animal at each bleed. This blood was allowed to clot overnight at 4° C., and then centrifuged for 30 min at 2000 g. The clarified serum was collected by aspiration and preserved by adding sodium azide at a final concentration of 0.1%.

2) Preparation of Leptin Affinity Columns Leptin affinity columns were prepared as follows. Sepharose 4B (available from Pharmacia Biotech, Piscataway, N.J.) was washed thoroughly in water by repeated filling, mixing, settling and decanting. After washing, the Sepharose 4B was suspended as a 50% slurry in 0.1 M carbonate buffer (pH 11). Cyanogen bromide (Sigma, St. Louis, Mo.) was dissolved to saturation at room temperature in DMF (Aldrich, Milwaukee, Wis.) and added to the Sepharose slurry in a 1:10 v/v ratio. The activation procedure was carried out on ice, and in a fume hood with constant pH monitoring. The pH was maintained at 11 by adding 10 N NaOH as necessary. The activated material was washed in a vacuum funnel, first with chilled water, and then with a chilled borate buffer. Recombinant human leptin was added at a maximum of 10 mg of protein per ml of packed volume of Sepharose. This material was allowed to stand for at least six hours at 4° C. to permit the conjugation reaction to go to completion. Prior to use, the conjugated Sepharose was blocked with 1 M glycine and loaded into a column that was suitable for affinity purifying or cross-absorbing serum antibodies. Recombinant mouse leptin columns were prepared in a corresponding manner.

3) Affinity Purification of Polyclonal Anti-leptin Antibodies

Anti-leptin antibodies were purified using the leptin affinity columns as follows. One liter of hyperimmune rabbit antiserum was diluted to two liters with BBS and passed over a leptin affinity column prepared as described above. The bound antibody was eluted using 0.1 M glycine-HCl (pH 3.0), followed by 0.1 M glycine-HCl (pH 2.0), and followed by 0.1 N HCl containing 0.1 M NaCl. The eluted antibody was neutralized by adding excess BBS. F(ab')2 fragments were generated from the eluted antibody by dialyzing the antibodies into 0.1 M acetate buffer (pH 4.5), adding pepsin at a ratio of 2–3 mg per 100 mg of antibody, and incubating the mixture for between 4–18 hours at temperatures ranging between room temperature and 37° C. After incubation, the mixture was neutralized and purified by passage through a column of immobilized protein G, and then by passage through a column of Sephadex G-200.

4) Preparation of Anti-leptin Affinity Columns

Anti-leptin affinity columns were prepared using the purified anti-leptin antibodies in a manner corresponding to the preparation of leptin affinity columns, described above.

5) Purification of Leptin Containing Material from Human Blood

Leptin containing material was separated from human blood samples using the anti-leptin affinity columns as follows. Human blood samples were obtained from patients undergoing a phlebotomy for disorders unrelated specifically to obesity. The samples were initially collected using a variety of procedures, including with and without heparin, sodium citrate, and EDTA. Soluble serum and plasma proteins in the samples were separated from cellular material by centrifugation at 1000–2000 g for 30–60 minutes. The soluble fraction was decanted off and the cellular material was discarded. The serum was pooled and passed over the anti-leptin affinity columns containing immobilized rabbit anti-leptin antibody prepared as described above. The bound antibody was eluted using 0.1 M glycine-HCl (pH 3.0), followed by 0.1 M glycine-HCl (pH 2.0), and followed by 0.1 N HCl containing 0.1 M NaCl. The eluted leptin was neutralized by the addition of an excess of BBS and was concentrated by ultrafiltration using a pressurized stirred cell concentrator equipped with a 10 K cutoff membrane (Amicon, Beverly, Mass.).

6) Analysis of Material Containing Human Leptin

The material containing human leptin that was separated using the anti-leptin affinity columns was divided into analytical and preparative portions and analyzed by gel filtration by passage through Superose 6 and Superose 12 (Pharmacia, Piscataway, N.J.). The Superose was packed into preparative glass FPLC columns which were hooked together in series, and pumped at 1 ml/min using standard HPLC equipment (SSI, State College, Pa.). The columns used to analyze the analytical portion were equilibrated with phosphate buffered saline (pH 7.2). Some columns used to analyze the preparative portion were equilibrated with neutral pH, nondissociating buffer (0.34 M Borate buffered saline) similar to the analytical portion, while other of the columns used to analyze the preparative portion were equilibrated with acidic pH, mild, dissociating buffer (0.1 M HCl containing 0.1 M NaCl). The resultant fractions produced by the gel filtrations were collected in 1 ml aliquots. The preparative fractions were further evaluated for immunoreactive material by direct ELISA.

Referring now to FIG. 1, there is shown a continuous trace, gel filtration profile under neutral pH and monitored at 280 nm, showing the molecular weight distribution of the analytical portion. As can be seen, the material eluted in fractions represented by a tall high molecular weight peak, a second tall, intermediate weight peak, and a small, low molecular weight peak. Based on the known weight of recombinant leptin, if free leptin were present in the preparation it would have eluted in fractions corresponding to the low molecular weight peak. This analysis appeared to indicate that the human blood borne leptin which eluted from the column was partly free, and partly bound directly to two carriers, or alternately partly free, partly bound directly to a carrier and partly indirectly bound through the carrier to a larger aggregate.

Figure 2:
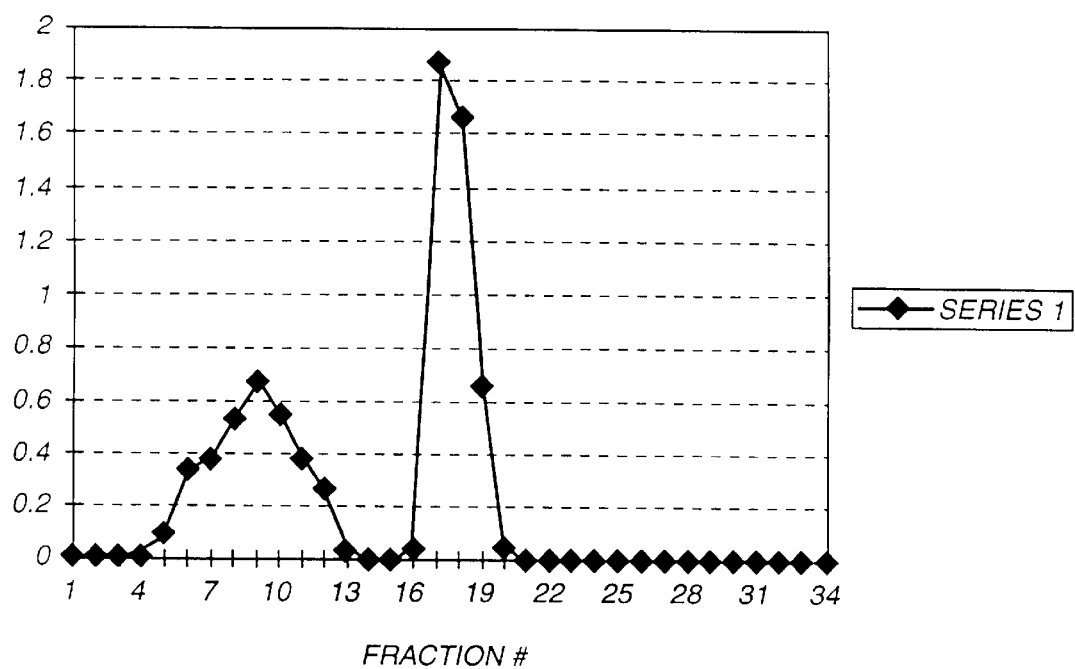
FIG. 2 is a semi-continuous plot of immunoreactivity versus elution volume (fraction number) of fractions of human serum collected from the eluate of the gel filtration columns under nondissociating conditions (neutral phase conjugation)

Referring now to FIG. 2, there is shown a semi-continuous plot of immunoreactivity versus elution volume (fraction number) of fractions collected from the eluate of the gel filtration columns under nondissociating conditions (neutral pH). The plot shows how immunoreactive leptin was partitioned along with the proteins which were separated by size by the gel filtration column under nondissociating conditions (neutral pH). The level of immunoreactive leptin in each fraction was measured by direct binding ELISA probed with a biotinylated affinity purified polyclonal rabbit anti-human leptin antibodies. As can be seen, immunoreactive leptin eluted in fractions corresponding to higher molecular weights. Based on the known molecular weight of recombinant leptin, free leptin would have eluted from the column throughout fractions 32–34. The apparent lack of free leptin in these fractions suggested that variable proportions of leptin in normal, nonobese, humans is substantially bound rather than free.

Figure 3:
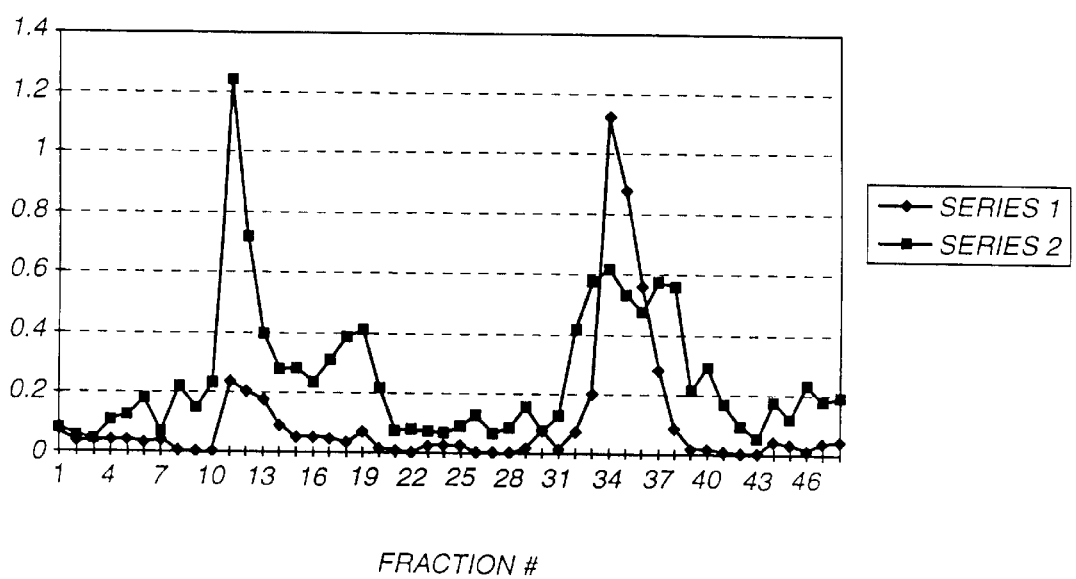
FIG. 3 is a semi-continuous plot of immunoreactivity versus elution volume (fraction number) of fractions of human serum collected from the eluate of the gel filtration columns under dissociating conditions (acidic phase conjugation)

Referring now to FIG. 3, there is shown a semi-continuous plot of immunoreactivity versus elution volume (fraction number) of fractions collected from the eluate of the gel filtration columns under dissociating conditions (acidic pH). The plot shows how immunoreactive leptin was partitioned along with the proteins which were separated by size by the gel filtration column under dissociating conditions (acidic pH). The level of immunoreactive leptin in each fraction was measured using a polyclonal rabbit, anti-human leptin antibody-based immunoassay (closed squares) and a monospecific, polyclonal antibody-based assay (closed diamonds). The monospecific, polyclonal antibody was raised to a synthetic peptide having an amino acid sequence common to mouse and human leptin but not found in known mouse or human proteins. As can be seen, under dissociating conditions, there was a decrease in the level of immunoreactive leptin in the higher molecular weight fractions compared with nondissociating conditions, (especially in the intermediate weight peak shown in FIG. 1). Further, immunoreactive leptin appeared in fractions 33–37, which overlapped with the fractions containing material of a molecular weight which corresponds to the known molecular weight of recombinant leptin. Further, the monospecific, polyclonal antibody (closed diamonds) was virtually unable to detect leptin in the high molecular weight fractions or to detect fragments which migrated to positions of lower molecular weight than intact leptin. Therefore, the monospecific, polyclonal anti-recombinant leptin antibodies appeared to have specificity for a region of leptin that was sensitive to degradation when leptin is fragmented, and that was also involved in binding with a substance of higher molecular weight or close enough to a region responsible for binding a substance to cause steric hindrance with respect to the binding of the anti-leptin antibodies..

These analyses implied that leptin in the human blood samples was, at least in part associated with one or more substances having a higher molecular weight than free leptin in normal human serum. The analyses also implied that the association between leptin and the substance was at least in part noncovalent since some free leptin dissociated from the complex under mild dissociating conditions. This material that was apparently binding leptin was initially labeled "leptin binding substance."

Figure 4:
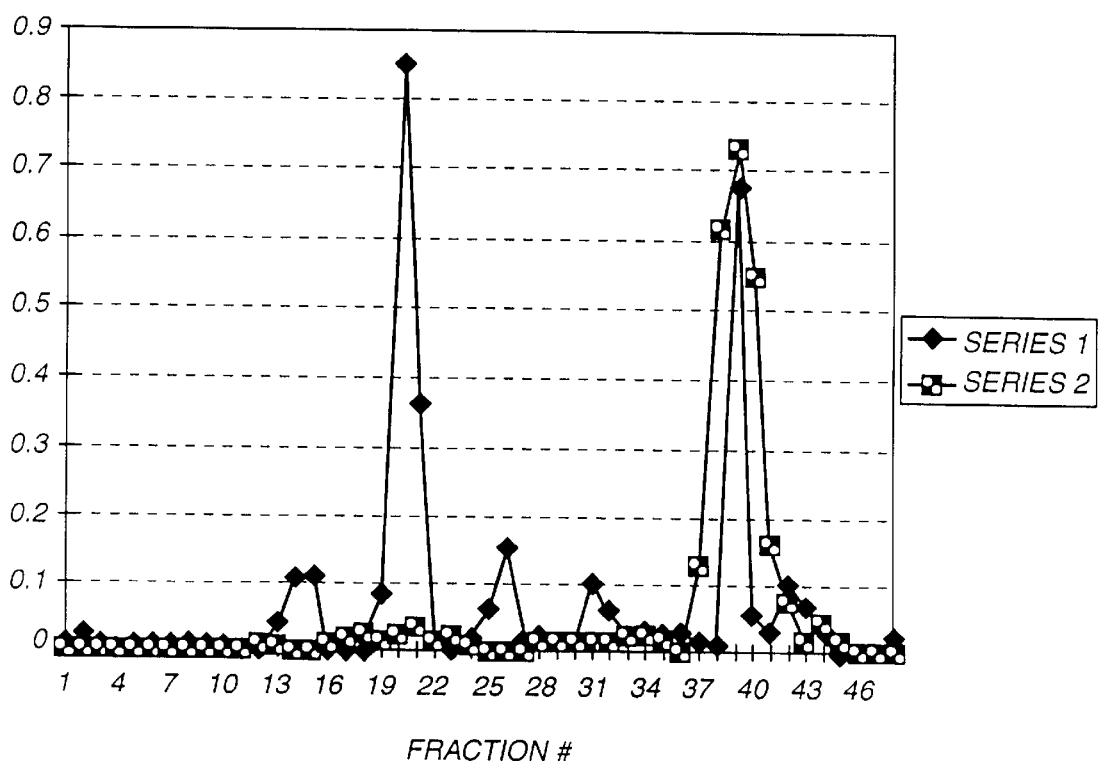
FIG. 4 is a semi-continuous plot of immunoreactivity versus elution volume (fraction number) of fractions of mouse serum and human serum collected from the eluate of the gel filtration columns under dissociating conditions (acidic phase conjugation)

7) Analysis of Mouse Serum Leptin Form and Comparison to Human Serum Leptin Form In order to determine whether mouse leptin was also associated with a binding substance in normal mouse serum, the processes described above used to analyze leptin from human blood samples were repeated using rabbit anti-mouse-leptin antibodies, and commercially available normal mouse serum (Bioproducts, Indianapolis, Ind.). The results were compared with corresponding analyzes for human blood samples. The eluted material was analyzed in a manner corresponding to that which produced FIG. 1 and the resulting profile (not shown) was substantially identical to that shown in FIG. 1. Further, the eluted material was fractionated and tested in a manner corresponding to that which produced FIG. 2 and the resulting graph (not shown) was also substantially identical. The material was further fractionated and tested in a manner corresponding to that which produced FIG. 3 and these results are shown in FIG. 4, which is a semi-continuous plot of immunoreactivity versus elution volume (fraction number) of fractions collected from the eluate of the gel filtration columns under dissociating conditions (acidic pH) for mouse blood (open diamonds). A profile of human serum derived leptin containing material is overlaid for comparison.

As can be seen in FIG. 4, under dissociating conditions, immunoreactive low molecular weight (unbound) mouse serum leptin eluted from the column in the same numbered fractions (36–41) (closed diamonds) as did immunoreactive human serum leptin (open squares). One difference observed was that the monospecific polyclonal antibody used as the probe in this assay for immunoreactive leptin detected mouse leptin in the high molecular weight fractions which implied a difference in the physical interaction between mouse leptin and the mouse leptin binding substance in the mouse serum compared with the interaction between human leptin and the human leptin binding substance (results discussed above).

8) Initial Isolation, Purification and Molecular Weight Characterization of Leptin Binding Substance In order to characterize the leptin binding substance, it was first purified from human serum as follows. Human blood samples were obtained from multiple donors undergoing a phlebotomy for disorders unrelated to obesity. Soluble serum and plasma proteins were separated from cellular material by centrifugation at 1000–2000 g for 30–60 min. The soluble fraction was decanted off and the cellular material was discarded. The serum from the multiple donors was pooled and passed over leptin-affinity columns containing immobilized recombinant human leptin. The bound material was eluted using a 0. 1% solution of SDS prewarmed to 37° C. in order to assure complete dissociation of the noncovalent complex which formed between the immobilized recombinant leptin and the serum derived leptin binding substance. The eluted material was concentrated and excess SDS was removed by repeated diafiltration in a borate buffered saline also prewarmed to 37° C. using stirred cell equipment and a 10 kDa pore size ultrafilter (Amicon, Beverly, Mass.). The eluate was then subjected to FPLC analysis and purification in a manner corresponding to the FPLC analysis of blood-derived leptin, described above.

Figure 5A:
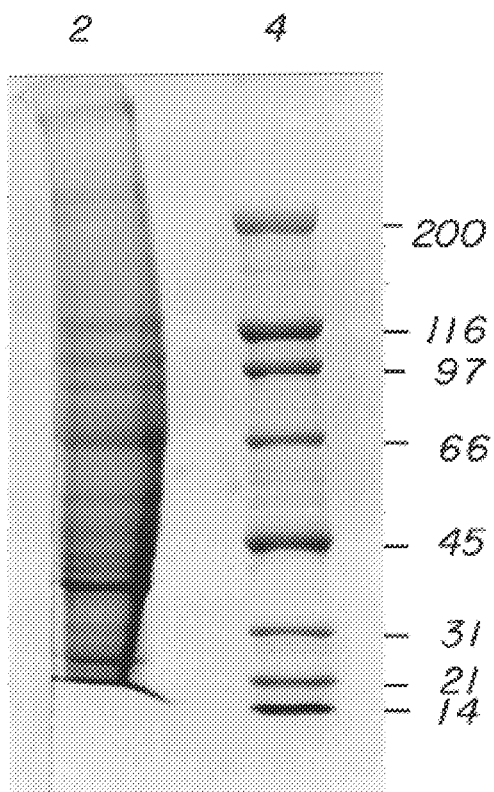
FIG. 5 is an SDS-PAGE analysis of the material recovered from a recombinant human leptin affinity column showing the band of the presumed leptin binding substance in the region of 80 kDa under non-reducing conditions (FIG. 5A, left) and in the region of 40kDa. under reducing conditions (FIG. 5B, right)
Figure 5B:
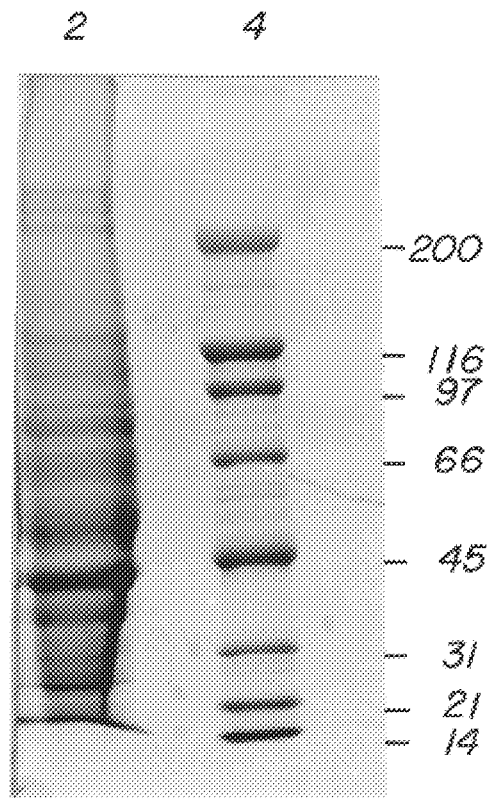

The purified material was analyzed by SDS-PAGE on 5–15% gradient gels using standard commercially available equipment (Biorad, Richmond, Calif.) according to methods as will be understood by those with skill in the art with reference to the disclosure herein. The results are shown in FIG. 5. The material was analyzed under both nonreducing (FIG. 5A, left and reducing conditions (FIG. 5B, right). The gels were stained with Comassie Blue, destained, and dried all according to standard methods. As can be seen, there was a predominant band in the region of 80 Kd under nonreducing conditions (FIG. 5A, left) and of 40 Kd under reducing conditions (FIG. 5B, right), lanes 1 and 3 (from left to right). Lanes 2 and 4 represent molecular weight markers.

9) Affinity Purification and Cross Absorption of Rabbit Anti-human Leptin Binding Substance Antibodies Polyclonal rabbit, anti-human leptin binding substance antibodies were produced to the material present in the 40 KDa band, isolated as described above, in a manner corresponding to the production of polyclonal antibodies to leptin, also described above. Leptin binding substance affinity columns were produced in a manner corresponding to the production of leptin affinity columns, described above, using the same material present in the 40 KDa bands, described above, which was bound to cyanogen bromide activated Sepharose. The rabbit anti-human leptin binding substance antibodies were affinity purified on the leptin binding substance columns, in a manner corresponding to that described above for the antibodies to leptin.

In addition to affinity purification, the rabbit anti-human leptin binding substance antibodies were cross-absorbed against a large panel of purified human proteins including immunoglobulins, collagens, and albumin. The proteins were extracted from a variety of human tissues, including serum, in an attempt to assure that naturally occurring and potentially problematic antibodies in the rabbit serum were discarded from the final preparation and that antibodies raised unintentionally in the rabbits in response to the minor contaminants which might be present in the isolated leptin binding substance were also removed and discarded. The level of cross-reactive antibody depletion was monitored by calculating the amount of protein lost following each pass and by monitoring the amount of protein which bound to the columns during the subsequent washing and recycling. As expected, only a small fraction of the total antibody bound to the affinity column and most of the antibody which was lost during the cross-absorption was lost during the first absorptions indicating nonspecific cross reactions.

10) Biotinylation of Anti-leptin Binding Substance Antibody and HRP Conjugation of Streptavidin Long chain NHS biotin (Sigma, St. Louise, Mo.), was dissolved in DMF (Aldrich, Milwaukee, Wis.) and added to the anti-human leptin binding substance antibody at a molar ratio of approximately 15:1. The mixture was incubated for 30–60 minutes and free biotin was removed by gel filtration on Sephadex G-25. The conjugated material was diluted into 1% BSA at a final concentration of 1 mg/ml. Streptavidin at a concentration of 10 mg/ml was dialyzed into carbonate buffer (pH 9.5). HRP having a concentration of 10 mg/ml was dialyzed into carbonate buffer at (pH 8.0). Sodium periodate was added to the HRP at approximately 1 $\mu$g/ml. After 2–4 hours at room temperature, the periodate was inactivated by adding of 1/6 w/v or dry G-25 and the dialyzed streptavidin was added to the mixture. The HRP/streptavidin mixture was allowed to stand for between 18 and 24 hours. The conjugate was then stabilized with sodium borohydride having a concentration of 1 $\mu$g/ml, purified by gel-filtration on Superose 6 in order to exclude over and under conjugated material, and diluted into 1% BSA at a final concentration of 1 mg/ml.

11) SDS-PAGE and Western Blotting of Human Serum with Anti-leptin Binding Substance The specificity of the antibody raised to the human leptin binding substance was first analyzed by western blotting of normal human serum as follows. One hundred $\mu$l of normal human serum was run on 5–15% SDS-PAGE as described above under both reducing and nonreducing conditions using standard methods and equipment (Biorad, Richmond, Calif.). The resulting slab gels were removed from the apparatus and the separated proteins were transferred to nitrocellulose blotting membranes (Costar, Cambridge, Mass.) using a standard submersion tank electrophoretic transfer apparatus (Biorad, Richmond, Calif.). Each gel was blotted twice. The blotted nitrocellulose membranes were lifted from the slab gel and transferred to borate buffered saline containing 0.1% gelatin and 1% BSA, and 0.1% tween-20 (BMB, Indianapolis, Ind.). The slab gel was transferred to a solution of Comassie Blue. The blots were incubated for 2 hours, washed several times, and the primary antibody was added, all in the same buffer. Unprocessed antiserum was added to one set of reduced and nonreduced blots at a final dilution of 1:1000. The affinity purified, cross-absorbed, and biotinylated anti-human leptin binding substance antibodies were added to the other set of blots at a final dilution of 1:10,000 from the original 1 mg/ml stock. After incubation overnight, both sets of blots were washed again. The first set of blots was counterstained with biotinylated goat anti-rabbit IgG also diluted 1:10,000 (human serum absorbed from Brookwood Biomedical, Birmingham, AL, also available from Sigma, St. Louis, Mo.) for 2 hours. Both sets of blots were again washed, incubated with a 1:1,000 dilution of alkaline phosphatase conjugated streptividin (Brookwood Biomedical, Birmingham, Ala., also available from Sigma, St. Louis, Mo.) for an additional 2 hours, and washed again. Finally, the blots were transferred to 100 ml of substrate buffer consisting of 0.1 M carbonate buffer (phase conjugation 9.5) containing 15 mg of BCIP and 30 mg of NBT (Molecular Probes, Eugene, Oreg.). Color was allowed to develop and was monitored visually. The blots were then air dried.

Figure 6A:
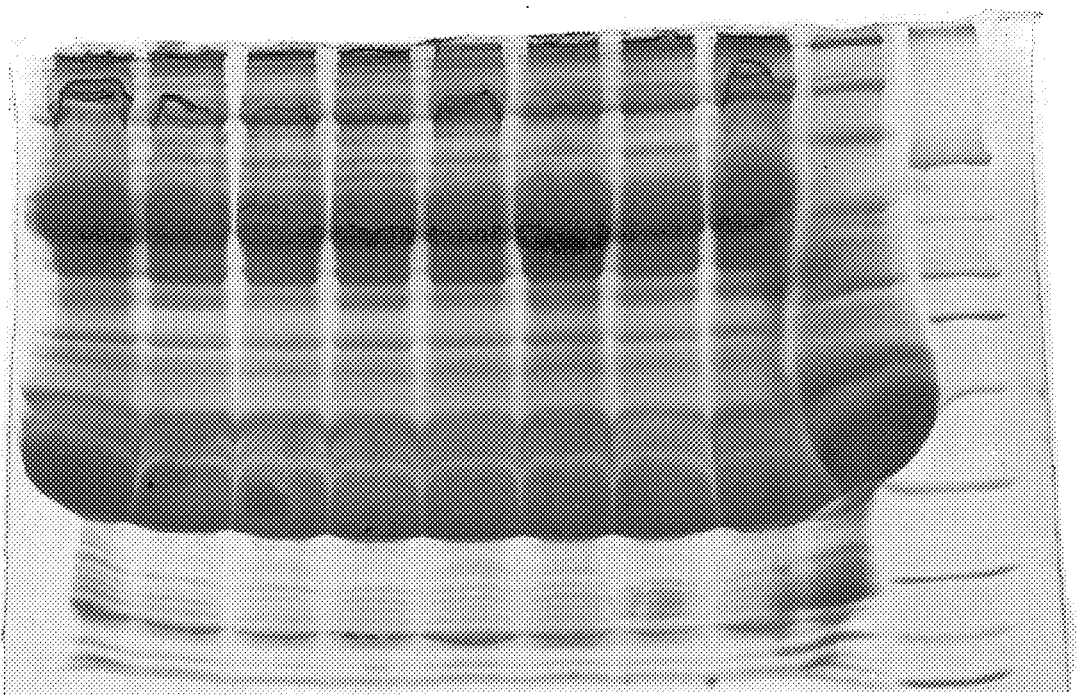
FIG. 6 is a 5–15% SDS-PAGE analysis of whole, unfractionated normal human serum from ten different normal, nonobese individuals under nonreducing conditions (FIG 6A, upper and reducing conditions (FIG. 6B, lower)
Figure 6B:
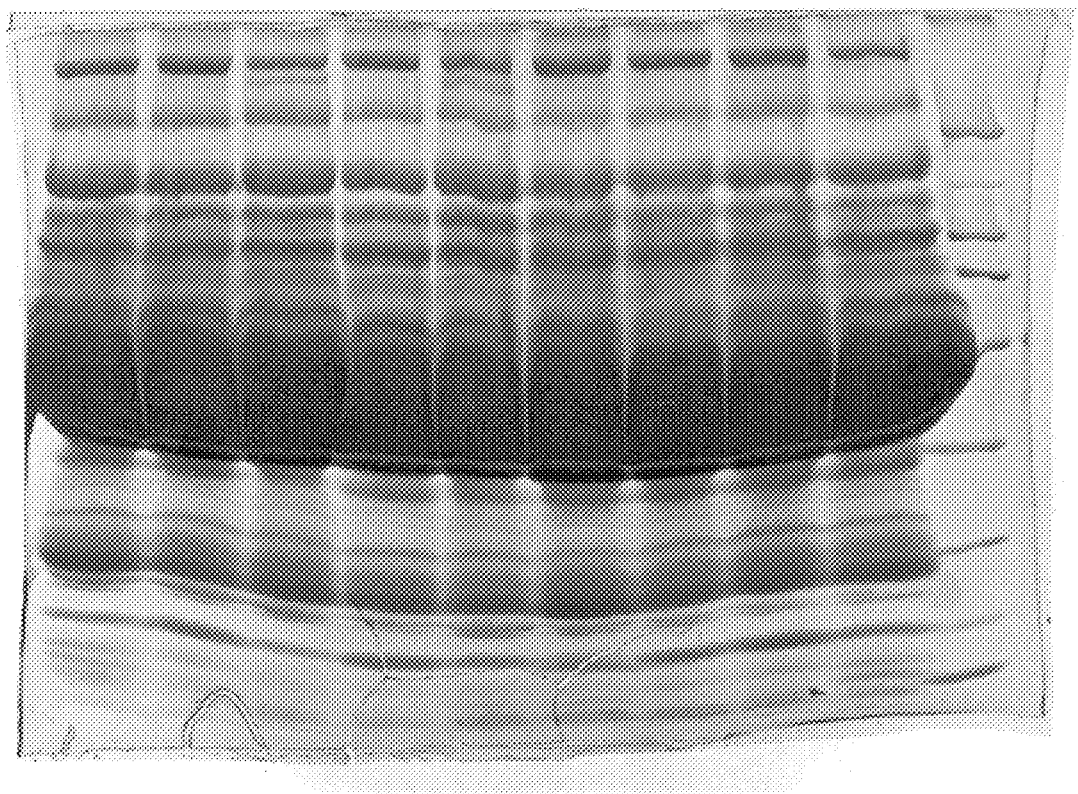

Referring now to FIG. 6, there is shown a Comassie Blue stained, 5–15% SDS-PAGE analysis of the whole, unfractionated normal human serum from ten different normal, nonobese individuals under reducing conditions (FIG 6A, upper) and reducing conditions (FIG. 6B, lower).The rightmost lane contains molecular weight standards. As can be seen, each lane containing human serum presents a pattern similar to the other lanes and displays a significant albumin band and significant immunoglobulin bands. In addition, there are present a large number of less prominent, high and low molecular weight bands corresponding to various normal human serum proteins.

Figure 7A:
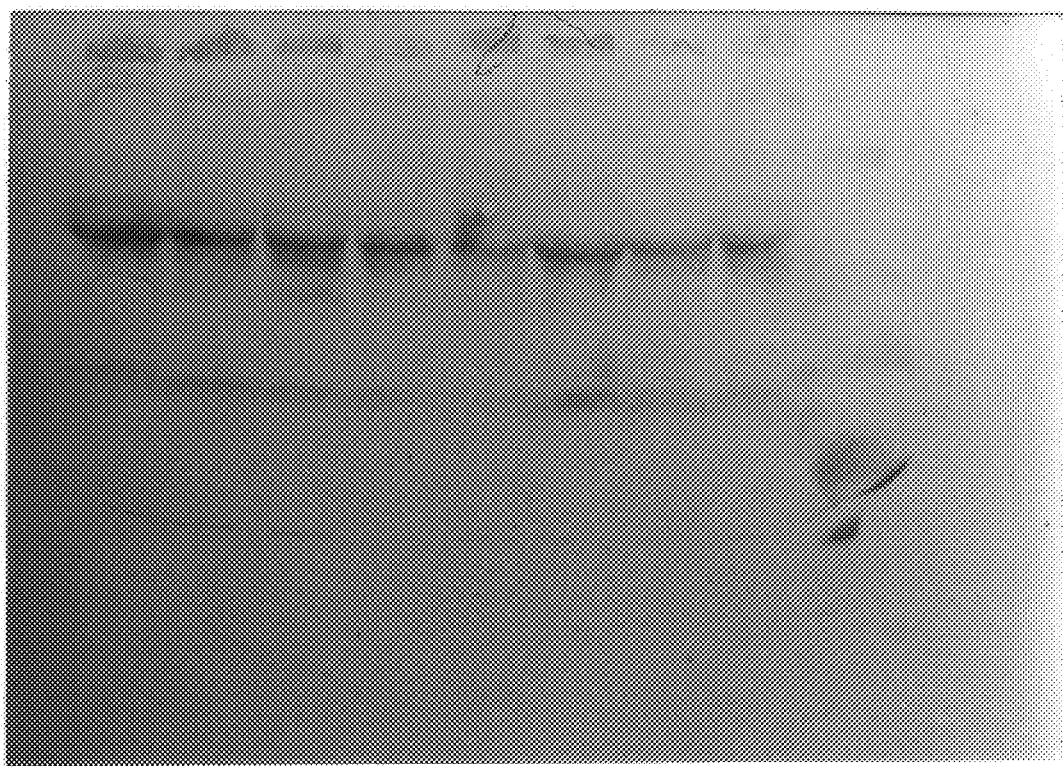
FIG. 7 is a nitrocellulose immunoblot of the SDS-PAGE gel shown in FIG. 6, using unfractionated and unprocessed rabbit anti-leptin binding substance anti-serum under both reducing (FIG. 7A, upper) and nonreducing (FIG. 7B, lower) conditions.
Figure 7B:
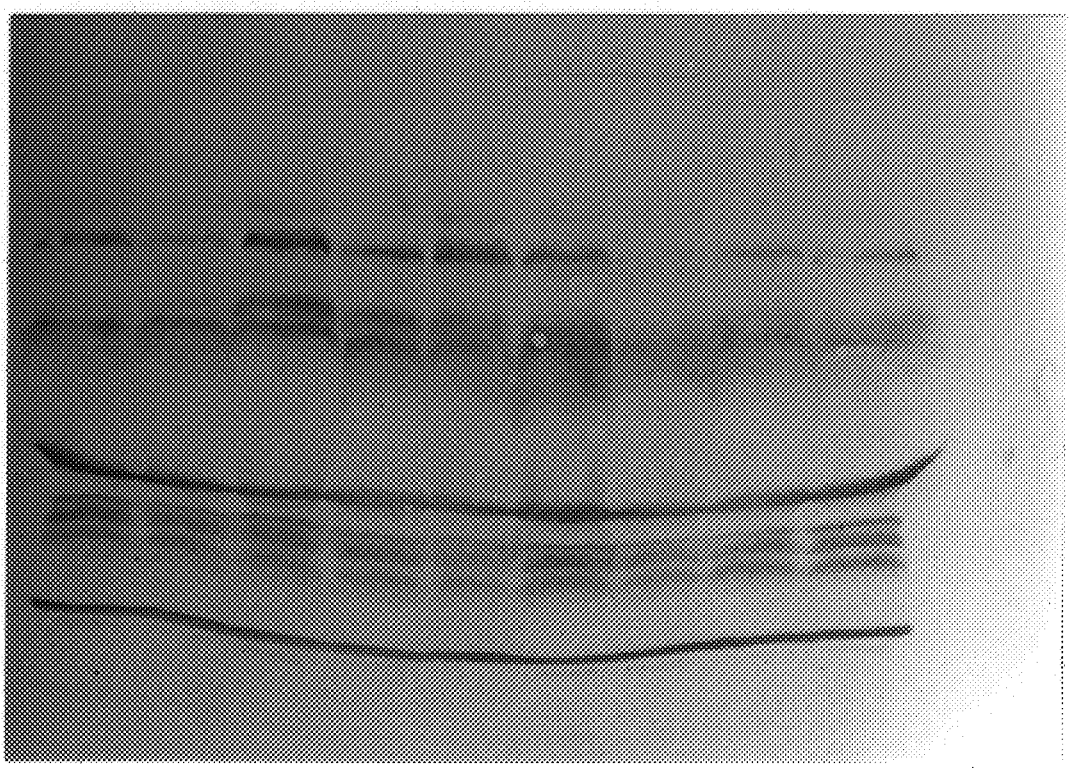

Referring now to FIG. 7, there is shown a nitrocellulose immunoblot of an SDS-PAGE gel as shown in FIG. 6, using unfractionated and unprocessed rabbit anti-leptin binding substance anti-serum generated as above, under both nonreducing (FIG. 7A, upper) and reducing (FIG. 7B, lower) conditions. As can be seen, the antiserum displayed significant cross-reactivity with a variety of serum proteins on both the reduced and nonreduced immunoblots.

Figure 8A:
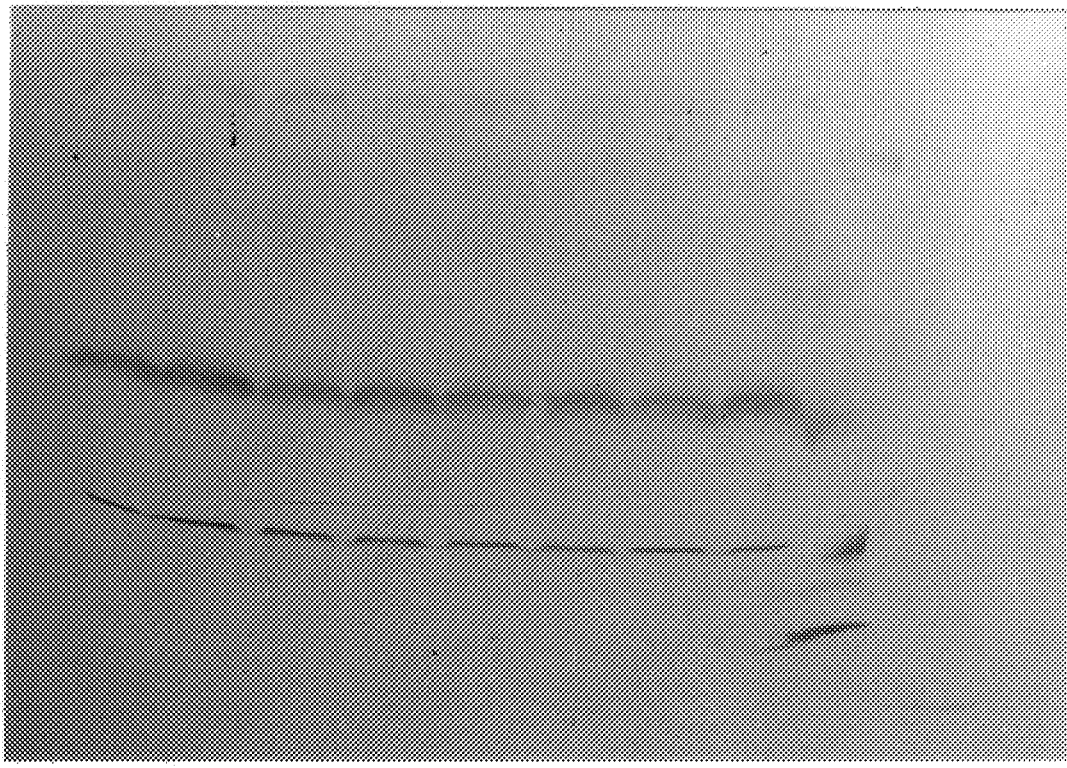
FIG. 8 is a nitrocellulose immunoblot of the SDS-PAGE gel shown in FIG. 6, using the affinity purified and cross-absorbed rabbit anti-human leptin binding substance antibodies under nonreducing conditions (FIG. 8A, upper) and reducing conditions (FIG. 8B, lower)
Figure 8B:
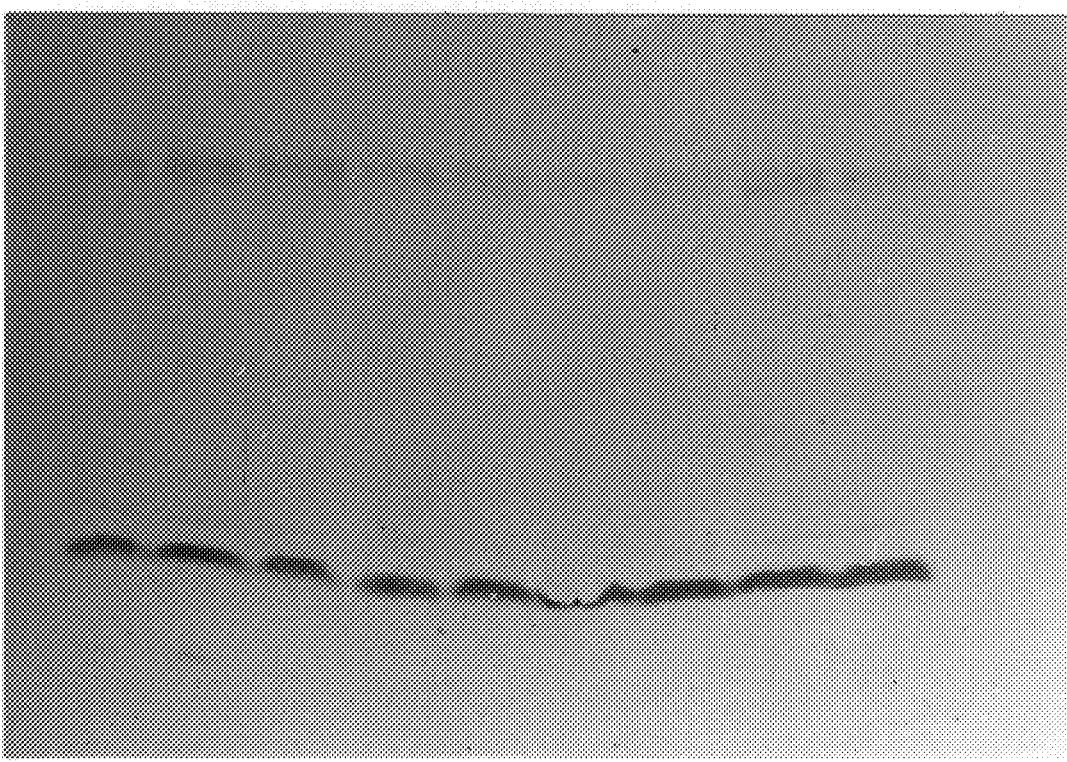

Referring now to FIG. 8, there is shown a nitrocellulose immunoblot of an SDS-PAGE gel as shown in FIG. 6, using the affinity purified and cross-absorbed rabbit anti-human leptin binding substance antibodies prepared as above, under nonreducing conditions (FIG. 8A, upper) and reducing conditions (FIG. 8B, lower). As can be seen, the antibody displayed specificity for a component of normal human serum with an apparent molecular weight of approximately 80 KDa and another component with an apparent molecular weight of approximately 40 Kd under nonreducing conditions (FIG. 8A, upper). Under reducing conditions (FIG. 8B lower), the antibody showed specificity for one component with an apparent molecular weight of approximately 40 KDa. This suggests that leptin binding substance can exist either as a monomer or as a dimer crosslinked by disulfide bonds.

12) Confirming the Identity of Leptin Binding Substance though Amino Acid Sequencing In order to confirm the identity of leptin binding substance, aliquots of leptin affinity column eluate were concentrated, dialyzed against saline, and further processed by gel filtration on Superose 12. These steps were taken both in order to remove excess SDS for better resolution on SDS-PAGE and to remove contaminants which could potentially make it difficult to remove the 40 KDa band for extraction and N-terminal amino acid sequencing. The material eluted as a somewhat broad band from the Superose 12 column and four fractions were collected throughout the elution which was monitored at 280 nm. These fractions were analyzed and the cleanest fraction was chosen for sequencing.

Figure 9:
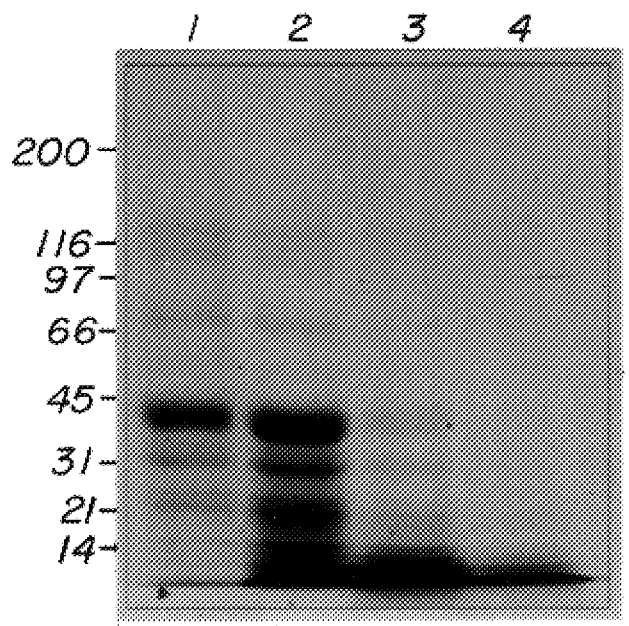
FIG. 9 is a 5–15% SDS-PAGE analysis under reducing conditions of four fractions that eluted from a recombinant human leptin affinity column following downstream gel purification.

Referring now to FIG. 9, there is shown a Comassie Blue stained 5–15% SDSPAGE of each of the four fractions run under reducing conditions in individual lanes. The gel shows four individual lanes which correspond to the four fractions collected sequentially from the leptin affinity gel-filtration column. Lane 1 (leftmost) corresponded to the fraction with the highest molecular weight, lane 4 (from the left) corresponded to the fraction with the lowest molecular weight and lanes 2 and 3 corresponded to the fractions of intermediate weight. As can be seen, lanes 1 and 2 show a predominant band in the molecular weight region of 40 KDa, the weight corresponding to the leptin binding substance, and lanes 3 and 4 show predominantly low molecular weight contaminating materials. Based on this visual assessment, the material shown in lane 1 which corresponds to the material in fraction 1 was sent for N-terminal amino-acid sequencing according to techniques well known to those with skill in the art. The sequencing revealed that leptin binding substance was apolipoprotein J, a substance previously known to have a variety of functions, but not previously known to have an association with leptin. The results of the analyses above are consistent with known characteristics of apolipoprotein J since apolipoprotein J is known to exist as a disulfide crosslinked homodimer with a monomeric size of 40 KDa and a dimeric size of 80 KDa. The 80 KDa Apolipoprotein J precursor is disulfide linked and post-translationally cleaved. The resulting 80 KDa molecule consists of a heterodimer between the apolipoprotein J alpha and beta chains, each of which is 40 KDa and derived from the same precursor. The monomers have been found to exist either as an alpha or a beta form having minor sequence differences. Apolipoprotein J is also known to associate with high molecular weight lipoprotein complexes (especially HDL). These characteristics of apolipoprotein J contributed to the confirmation that leptin binding substance was apolipoprotein J.

ASSAY OF BOUND AND UNBOUND LEPTIN

According to another aspect of the present invention, there is provided an immunoassay of bound and unbound leptin. The assay used ABTS as the substrate, and used two different signaling antibodies, one specific for human leptin and the other specific for apolipoprotein J. Both antibodies were conjugated to biotin and used in conjunction with HRP-streptavidin, prepared using techniques described above. As will be understood by those with skill in the art with reference to the disclosure herein, other signaling systems can be used, such as I-125, FITC, phycoerythrin, alkaline phosphatase, horseradish peroxidase, and B-galactosidase, other substrates could be used such as TMB, and OMPD, and various readout options are available for each of these systems.

Two sets of two flexible high protein binding 96 well ELISA plates (Costar, Cambridge, MA) were passively coated with polyclonal rabbit, anti-human leptin antibodies prepared as described above. Monoclonal antibody, fragments such as F(ab')2 fragments, or F(ab') fragments, or a combination of the two or more of these, with or without polyclonal antibodies, could also be used, as will be understood by those with skill in the art with reference to the disclosure herein. Further, other solid phases such as beads, membranes, particles, or tubes could also be used.

The rabbit anti-human leptin antibody was passively coated directly onto ELISA plates by adding 100 µl of a 10 µg/ml solution of the antibody diluted in 0.34 M borate buffered saline (phase conjugation 8.2) for 18–24 hrs. at 4° C. The plates were washed of excess unbound antibodies and blocked with 0.34 M borate buffered saline containing 0. 1% tween-20, 0.1 % gelatin, and 1% BSA. Twenty-four human serum samples were obtained, which included samples from seven patients with anorexia nervosa (#1–7), samples from five normal donors (#8–12), samples from eight obese Pima Indians (#13–20), and samples from four patients with Prader-Willi Syndrome (#21–24) (a congenital disease that causes obesity in the affected individuals). One hundred µl of each serum sample was added at dilutions of 1:2 and 1:20 in the above buffer to individual wells of the assay plate and allowed to incubate for 24 hrs at 4° C. The plates were again washed. One hundred µl of a 1:20,000 dilution (from a 1 mg/ml stock) of biotinylated anti-human leptin antibodies were added to one set of plates, while a similar dilution of biotinylated anti-human apolipoprotein J antibodies (from a similar 1 mg/ml stock) was added to the other set of plates. The plates allowed again to incubate for 2 hrs at room temperature. They were washed again and 100 µl of a 1 :10,000 dilution of HRP-streptavidin was added and incubated for 2 additional hours. Finally, the plates were washed and ABTS substrate was added (BMB, Indianapolis, Ind.). After 10 minutes, the plates were read using an automatic plate reader (Titertec, ICN, Costa Mesa, Calif.).

Figure 10:
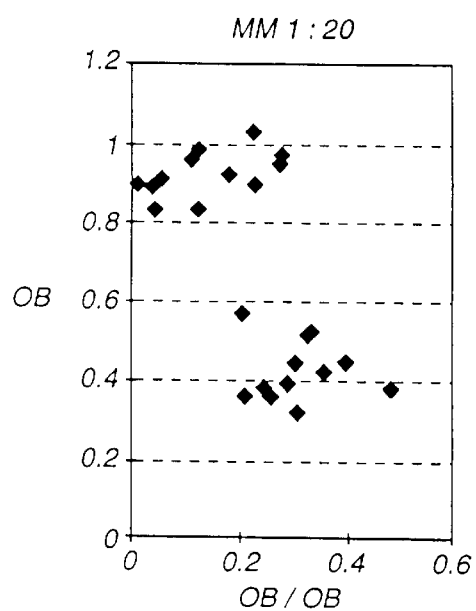
FIG. 10 shows two scatter diagrams produced by assays of leptin levels associated with apolipoprotein J and unassociated with apolipoprotein J in 24 subjects at two dilutions.
Figure 10:
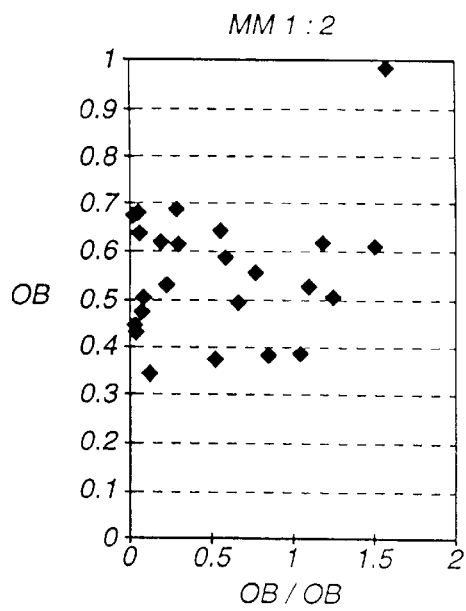

Referring now to FIG. 10, there is shown a scatter diagram summary of the results of these 2 parallel assays. The data are presented in terms of optical density (OD) units. Coordinates are given for anoretic (AN), normals (NO), obese (OB) and Prader-Willi (PW) subjects. The optical density measurements shown along the X axis were from the symmetrical assay based on the use of the anti-leptin antibodies to capture and biotin labeled anti-leptin antibodies to signal. These measurements represent a measure of the amount of leptin not associated with apolipoprotein J. The optical density measurements shown along the Y axis were from the asymmetrical assay based on the use of anti-leptin antibodies to capture and labeled anti-apolipoprotein J antibodies to signal. These measurements represent a measure of the amount of leptin associated with apolipoprotein J.

Referring to the left chart, FIG. 10A, there is shown the data generated using the above ELISA formats and the human serum samples tested at a 1:20 dilution. It can be seen that two distinct distributions are apparent. One distribution (upper left) corresponded to data from normal and lean anoretic patients. A second distribution (lower right) corresponded to data from obese and Prader-Willi patients. As can be appreciated from the data, a substantial portion of serum leptin is associated with apolipoprotein J in normal and lean anoretic individuals, but far less serum leptin in obese individuals is associated with apolipoprotein J.

Referring now to the right chart FIG. 10B, there is shown the data generated using the above ELISA formats and the human serum samples tested at a 1:2 dilution. It can be seen that two distributions are apparent. One distribution (far left) corresponded to data from normal and lean anoretic patients. A second distribution (middle to right) corresponded to data from obese and Prader-Willi patients. As can be appreciated from the data, a substantial portion of serum leptin is associated with apolipoprotein J in normal and lean anoretic individuals since values along the Y axis remained higher than those along the X axis. Further, the low levels of unbound leptin in the serum of normal and lean anoretic individuals appear to compete more efficiently for binding to the anti-leptin antibody than bound leptin since the values along the Y axis are lower at the 1:2 dilution than at the 1:20 dilution.

The data also appears to indicate that the symmetrical assay used herein is affected by steric hindrance when a substantial portion of leptin is bound to apolipoprotein J. Such steric hindrance probably accounts for discrepancies between the serum leptin levels obtained in the symmetrical assay herein and results derived using other immunoassay formats including both immuoprecipitation and semi-quantitative immunoblotting, and single site competitive radioimmunoassays. Hence, the known assays for leptin levels probably measure total leptin levels in obese individuals more accurately (because leptin is largely unbound to apolipoprotein J in such individuals) than leptin levels.

Further, the asymmetrical assay format used herein appears to be a more accurate measure of total serum leptin levels in normal and lean anoretic individuals than known assays for leptin, because the majority of the leptin appears to be associated with apolipoprotein J in such individuals. In obese individuals, however, the asymmetrical assay does not appear to measure total serum leptin levels because the majority of the serum leptin in obese individuals does not appear to be associated with apolipoprotein J in such individuals.

Therefore, previously used assays appear to have been underestimating the amount of total serum leptin in normal individuals due to the assays' lack of sensitivity for measuring leptin associated with apolipoprotein J. However, previously used assays more accurately measured the amount of total serum leptin in obese individuals because only a small portion of leptin is associated with apolipoprotein J in such individuals.

Thus, it appears that the defect in the endogenous leptin pathway in obese individuals is not related solely to total leptin levels, but to the form of circulating leptin, whether bound or unbound to apolipoprotein J.

As used in the following sections and claims, "leptin" encompasses biologically active variants of naturally occurring leptin, as well as biologically active fractions of naturally occurring leptin and variants thereof, and combinations of the preceding. As used herein, "apolipoprotein J" encompasses biologically active variants of naturally occurring apolipoprotein J, as well as biologically active fractions of naturally occurring apolipoprotein J and variants thereof, and combinations of the preceding.

COMPOSITIONS FOR DETECTING AND TREATING ABNORMALITIES IN THE ENDOGENOUS LEPTIN PATHWAY

In one embodiment, the present invention is a composition useful for diagnosing and treating abnormalities in the endogenous leptin pathway, such as physiological obesity. The composition comprises a purified form of leptin bound to apolipoprotein J. In a preferred embodiment, the composition consists essentially of leptin bound to apolipoprotein J. The leptin can be derived from natural sources or can be derived from recombinant sources, as will be appreciated by one of ordinary skill in the art with reference to the disclosure herein. In a preferred embodiment, the leptin is derived from a mammal, such as a human. The apolipoprotein J can be derived from natural sources or can be derived from recombinant sources, as will be appreciated by one of ordinary skill in the art with reference to the disclosure herein. In a preferred embodiment, the apolipoprotein J is derived from a mammal, such as a human.

The present invention further contemplates a pharmaceutical preparation for the treatment of abnormalities in the endogenous leptin pathway comprising a purified form of leptin bound to apolipoprotein J bound and including a pharmaceutically acceptable carrier. In another embodiment, there is provided a pharmaceutical preparation for the treatment of abnormalities in the endogenous leptin pathway consisting essentially of leptin bound to apolipoprotein J, and a pharmaceutically acceptable carrier.

In another embodiment, there is provided a pharmaceutical preparation for the treatment of abnormalities in the endogenous leptin pathway comprising apolipoprotein J and a pharmaceutically acceptable carrier. In a preferred embodiment, the pharmaceutical preparation consists essentially of apolipoprotein J and a pharmaceutically acceptable carrier. In another embodiment, there is provided a pharmaceutical preparation for the treatment of abnormalities in the endogenous leptin pathway consisting essentially of apolipoprotein J.

The present invention further includes a method of making the compositions according to the present invention. The method includes the steps of providing a substantially purified leptin, and binding the leptin to apolipoprotein J or providing a substantially purified leptin bound to apolipoprotein J. The leptin can be derived from natural or recombinant sources. The apolipoprotein J can be derived from natural or recombinant sources. Further, the method can include the step of adding a pharmaceutically acceptable carrier to the composition. Apolipoprotein J can be prepared, for example, by expressing it in insect cells using baculovirus, in bacterial cells, or in CHO cells.

METHODS OF DIAGNOSING AND TREATING ABNORMALITIES IN THE ENDOGENOUS LEPTIN PATHWAY

According to another aspect of the present invention, there is provided a method of diagnosing abnormalities in the endogenous leptin pathway in a subject mammal. The method comprises the steps of (a) determining an amount of apolipoprotein J in a test sample taken from the subject mammal, and (b) comparing the determined amount to a range of values for mammals with normal endogenous leptin pathways, where a determined amount greater than or less than the range of values indicates a diagnosis of an abnormality in the endogenous leptin pathway. According to another embodiment of the present invention, there is provided a method for diagnosing physiological obesity in a subject mammal comprising the steps of (a) determining an amount of apolipoprotein J in a test sample taken from the subject mammal, and (b) comparing the determined amount to a range of values for mammals with normal endogenous leptin pathways, where a determined amount less than the range of values indicates a diagnosis of physiological obesity. According to yet another embodiment of the present invention, there is provided a method for diagnosing abnormalities in the endogenous leptin pathway in a subject mammal comprising the steps of (a) determining an amount of leptin bound to apolipoprotein J in a test sample taken from the subject mammal, and (b) comparing the determined amount to a range of values for mammals with normal endogenous leptin pathways, where a determined amount greater than or less than the range of values indicates a diagnosis of an abnormality in the endogenous leptin pathway. According to another embodiment of the present invention, there is provided a method for diagnosing physiological obesity in a subject mammal comprising the steps of (a) determining an amount of leptin bound to apolipoprotein J in a test sample taken from the subject mammal, and (b) comparing the determined amount to a range of values for mammals without physiological obesity, where a determined amount less than the range of values indicates a diagnosis of physiological obesity.

According to another aspect of the present invention, there is provided a method of diagnosing abnormalities in the endogenous leptin pathway in a subject mammal comprising the steps of, first, determining at least one parameter in a test sample taken from the subject mammal selected from the group consisting of 1) an absolute amount of leptin bound to apolipoprotein J, 2) an absolute amount of leptin not bound to apolipoprotein J, 3) a percent of total leptin that is bound to apolipoprotein J, 4) a percent of total leptin that is not bound to apolipoprotein J, 5) the ratio of (an absolute amount of leptin that is bound to apolipoprotein J) to (an absolute amount of total leptin), 6) the ratio of (an absolute amount of leptin that is bound to apolipoprotein J) to (an absolute amount of leptin that is not bound to apolipoprotein J), and 7) the ratio of (an absolute amount of leptin that is not bound to apolipoprotein J) to (an absolute amount of total leptin). Next, the determined parameter is compared with a range of values for the parameter in the same type of mammal without abnormalities in the endogenous leptin pathway. A determined amount lesser or greater than the range of values indicates a diagnosis of an abnormality in the endogenous leptin pathway. The subject mammal in the determining step can be a human. In a preferred embodiment the test sample in the determining step can be selected from the group consisting of blood, serum, plasma, urine, and cerebral spinal fluid, however, any appropriate test sample is acceptable as will be understood by those with skill in the art with reference to the disclosure herein.

According to another aspect of the present invention, there is provided a method of treating abnormalities in the endogenous leptin pathway in a subject mammal comprising the step of administering to the subject mammal at least one treatment dose of consisting essentially of apolipoprotein J. According to another embodiment of the present invention, there is provided a method of treating abnormalities in the endogenous leptin pathway in a subject mammal comprising the step of administering at least one treatment dose of consisting essentially of apolipoprotein J and a pharmaceutically acceptable carrier.

According to yet another aspect of the present invention, there is provided a method of treating abnormalities in the endogenous leptin pathway in a subject mammal comprising the step of administering to the subject mammal at least one treatment dose of a composition according to the present invention. These compositions include compositions comprising leptin bound to apolipoprotein J and compositions consisting essentially of leptin bound to apolipoprotein J. The dose of the composition which includes leptin is preferably between about 0.1 and 10 mg leptin/kg body weight. The at least one dose can be at least one dose per day for at least about five days. In a preferred embodiment, the at least one dose is at least one dose per day for at least about 30 days. The dose or doses can be administered by a parenteral route, such as an intravenous or intraperitoneal route. The method can further comprise the step of serially an amount of leptin bound to apolipoprotein J in a test sample taken from the subject mammal after the step of administering. The method can further comprise the step of serially monitoring at least one of the following levels at least one time after the administering step: 1) an absolute amount of leptin bound to apolipoprotein J, 2) an absolute amount of leptin not bound to apolipoprotein J, 3) a percent of total leptin that is bound to apolipoprotein J, 4) a percent of total leptin that is not bound to apolipoprotein J, 5) the ratio of (an absolute amount of leptin that is bound to apolipoprotein J) to (an absolute amount of total leptin), 6) the ratio of (an absolute amount of leptin that is bound to apolipoprotein J) to (an absolute amount of leptin that is not bound to apolipoprotein J), 7) the ratio of (an absolute amount of leptin that is not bound to apolipoprotein J) to (an absolute amount of total leptin), and 8) a combination of the preceding.

METHOD AND KIT FOR DETERMINING THE PRESENCE OR AMOUNT OF LEPTIN THAT IS BOUND TO APOLIPOPROTEIN J

According to another aspect of the present invention, there is provided a method for determining the presence or amount of leptin that is associated with apolipoprotein J in a test sample. The comprises the steps of first, providing a support having a first binding substance thereon. The first binding substance is capable of binding leptin associated with apolipoprotein J to the support. Next, the support is contacted with the test sample, thereby allowing any leptin associated with apolipoprotein J in the test sample to bind to the support through the first binding substance. Then, the support is contacted with a second binding substance. The second binding substance is capable of binding to any leptin associated with apolipoprotein J that has bound to the support, or is capable of binding to the first substance only when leptin associated with apolipoprotein J has bound to the first binding substance. Then, the second binding substance is detected. The detected second binding substance correlates with presence or amount of leptin associated with apolipoprotein J.

In a preferred embodiment, the first binding substance is selected from the group consisting of an anti-leptin antibody, an anti-apolipoprotein J antibody, a fraction of an anti-leptin antibody, a fraction of an anti-apolipoprotein J antibody, a derivative of an antileptin antibody, a derivative of an anti-apolipoprotein J antibody and a combination of the preceding. In another preferred embodiment, the second binding substance is selected from the group consisting of an anti-leptin antibody, an anti-apolipoprotein J antibody, a fraction of an anti-leptin antibody, a fraction of an anti-apolipoprotein J antibody, a derivative of an antileptin antibody, a derivative of an anti-apolipoprotein J antibody and a combination of the preceding.

The present invention also contemplates a kit for performing the method for determining the presence or amount of leptin that is associated with apolipoprotein J in a test sample. In one embodiment the kit comprises a support having the first binding substance, and a container holding the second binding substance. In another embodiment, the kit comprises a container holding the first binding substance, and a container holding the second binding substance.

EXAMPLE I

Method of Diagnosing Physiological Obesity in a Human

According to the present invention, a subject mammal is diagnosed with physiological obesity. First, the amount of leptin bound to apolipoprotein J in a test sample taken from the blood of the subject human is determined. Next, the amount is compared with a range of values for humans without physiological obesity. A determined amount less than the known range of values indicates a diagnosis of physiological obesity.

EXAMPLE II

Method of Diagnosing Physiological Obesity in a Human

According to the present invention, a subject mammal is diagnosed with physiological obesity. First, the amount of leptin bound to apolipoprotein J in a test sample taken from the blood of the subject human is determined. Next, the amount of leptin that is not bound to apolipoprotein J in the test sample is determined. Then, the ratio of bound leptin to unbound leptin is calculated. Next, the ratio is compared with a range of values for the ratio in humans without physiological obesity. A determined amount less than the known range of values indicates a diagnosis of physiological obesity.

EXAMPLE III

Method of Treating a Human with Physiological Obesity

According to the present invention, a subject human having a provisional diagnosis of physiological obesity is treated by a method of treating physiological obesity. The subject human is administered doses of leptin bound to apolipoprotein J at a dose of 5 mg leptin/kg body weight intravenously, once a day for 30 days. The subject's blood levels of leptin bound to apolipoprotein J are serially monitored to determine if the administered dose is appropriate as indicated by normalization of the bound leptin level. The dose is adjusted in 1 mg leptin/kg body weight up or down as appropriate depending on the measured ratios until the level of bound leptin normalizes, and that dose is then maintained throughout the treatment period.

Although the present invention has been discussed in considerable detail with reference to certain preferred embodiments thereof, other embodiments are possible. Therefore, the spirit and scope of the appended claims should not be limited to the description of the preferred embodiments contained herein.

What is claimed is:

1. A composition consisting essentially of apolipoprotein J bound to leptin.

2. The composition according to claim 1, wherein the leptin is obtained from a recombinant source.

3. The composition according to claim 1, wherein the leptin is from a mammal.

4. The composition according to claim 1, wherein the leptin is from a human.

5. A composition comprising purified apolipoprotein J bound to leptin.

6. The composition according to claim 5, wherein the leptin is obtained from a recombinant source.

7. The composition according to claim 5, wherein the leptin is from a mammal.

8. The composition according to claim 5, wherein the leptin is from a human.

9. A pharmaceutical preparation comprising the composition of claim 5 and a pharmaceutically acceptable carrier.

10. A pharmaceutical preparation consisting essentially of apolipoprotein J bound to leptin, and a pharmaceutically acceptable carrier.

11. The preparation according to claim 10, wherein the leptin is obtained from a recombinant source.

12. The composition according to claim 10, wherein the leptin is from a mammal.

13. The composition according to claim 10, wherein the leptin is from a human.

* * * * *